United States Patent [19]

Yamamori

[11] Patent Number: 5,142,359
[45] Date of Patent: Aug. 25, 1992

[54] ELECTRONIC ENDOSCOPE

[75] Inventor: Katsuhiko Yamamori, Yokohama, Japan

[73] Assignee: Ikegami Tsushinki Co., Ltd., Tokyo, Japan

[21] Appl. No.: 611,682

[22] Filed: Nov. 13, 1990

[30] Foreign Application Priority Data

Nov. 27, 1989 [JP] Japan .................. 1-304836

[51] Int. Cl.⁵ .................. A61B 1/04; H04N 17/02
[52] U.S. Cl. .................. 358/98; 128/6; 358/10; 358/139
[58] Field of Search .................. 358/98, 139; 128/10, 128/6

[56] References Cited

U.S. PATENT DOCUMENTS

| 4,682,214 | 7/1987 | Sato | 358/10 |
| 5,078,150 | 1/1992 | Hara | 358/98 |

FOREIGN PATENT DOCUMENTS 61-96891  5/1961  Japan .

OTHER PUBLICATIONS

"Recent Advances in Broadcast Camera Design", Ryan, J. O.; IEE Conference Publication (International Broadcast Convention) 1980, pp. 27–30.

"Automated Set-up System for High Sensitive Handy Camera", Murakami, K. and Wakui, K., IEE Conference Publication (International Broadcast Convention), 1980, pp. 31–33.

Primary Examiner—Howard W. Britton
Attorney, Agent, or Firm—Spencer, Frank & Schneider

[57] ABSTRACT

An electronic endoscope that can automatically adjust the electronic characteristics of the processing amplifiers such as white balance, gamma balance, black level, or the like at optimum reference values. This is accomplished by selecting one of the plurality of the test-pattern charts so that the selected test-pattern chart, which represents one or more charateristics of the processing amplifiers to be adjusted, faces the tip of the probe of the endoscope, and by automatically setting control values of the video processing amplifiers in accordance with the selected chart by an auto-setup circuit so that the control values of the processing amplifiers agree with the reference values. Even technicians or doctors unfamiliar with operation of video processors can easily and accurately adjust color or the like of the endoscope.

5 Claims, 6 Drawing Sheets

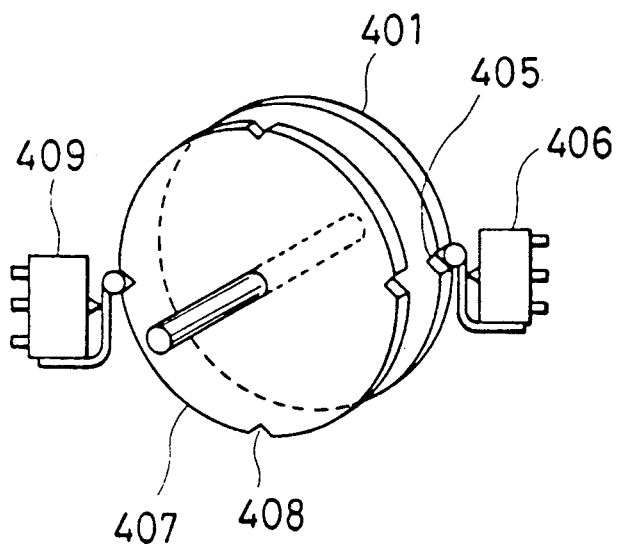
FIG. 4
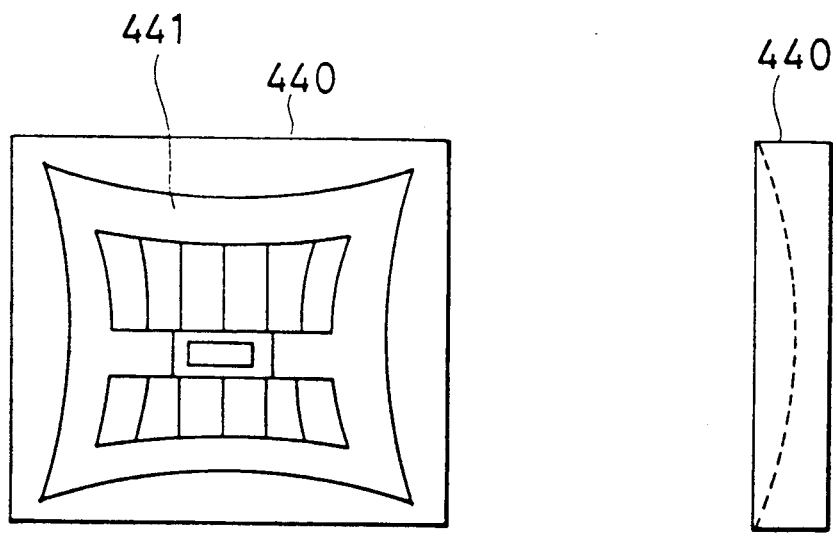 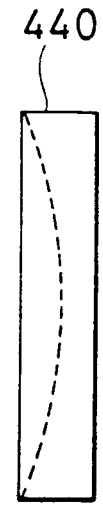
FIG.5A  FIG.5B

ELECTRONIC ENDOSCOPE

BACKGROUND OF THE INVENTION

1. Field of the Invention

The present invention relates to an electronic endoscope suitable for industrial or medical use.

2. Description of the Prior Art

When operating an electronic endoscope which incorporates a solid-state image pickup device at the tip of the probe thereof, it must be adjusted in advance so that best images can be reproduced. The adjustment of image quality is especially important with regard to medical electronic endoscopes because reproduced images are often used as materials for diagnosis.

Conventionally, the adjustment of an electronic endoscope in use is carried out beforehand by controlling white balance, at most, so that optimum images are reproduced. The white balance is adjusted by picking up a white sheet or the like as described in Japanese patent application laying-open No. 61-96891. Other fine adjustments such as gamma balance, black level, flesh-color, or blood color adjustment have not been performed.

The conventional electronic endoscopes have the following problems:

(1) Generally speaking, sizes of test-pattern charts which are used for adjusting electronic endoscopes are very small, for example about 23mm ×30mm for a small one, although the sizes vary in accordance with objective lenses incorporated in the tips of probes. As a result, image frame alignment between the tip of a probe of an electronic endoscope and a test-pattern chart which is performed by adjusting the distance or the angle between the tip of the probe and the test-pattern chart is very difficult.

(2) Accurate adjustment of an electronic endoscope is often hampered by external light added to the light from a light source. More specifically, the light emitted from the light source is generally transmitted from a video processor to the tip of the probe along the light guide so that the light is emitted from the tip of the probe to an object to be picked up. It is preferable that images be picked up by using this light alone. In practice, however, external light is often added to the light from the light source, thus preventing the accurate adjustment.

For these reasons, it is difficult for conventional electronic endoscopes to incorporate the test-pattern charts necessary for the fine adjustment of image quality. As a result, conventional electronic endoscopes cannot achieve the preliminary adjustment of the image quality. Furthermore, since the conventional electronic endoscopes are not provided with test-pattern charts, they cannot deal with the characteristic degradation of the video system or the light system thereof caused by deterioration with age. Consequently, they must be used without correcting the characteristic deterioration.

SUMMARY OF THE INVENTION

It is therefore an object of the present invention to provide an electronic endoscope that can solve the problems by incorporating various types of test-pattern charts, and enabling processing amplifiers of R, G and B channels to be controlled so that image quality can be adjusted beforehand in accordance with the test-pattern charts.

To accomplish the object, the present invention incorporates a plurality of test-pattern charts and a light source in the body of an electronic endoscope, such as a video processor, so that one of the test-pattern charts can be selected, and processing amplifiers of the R, G and B channels are automatically controlled in accordance with the selected test-pattern chart, and control values of the processing amplifiers are set at predetermined reference values so that the outputs of the processing amplifiers are adjusted according to the selected test-pattern charts.

More specifically, the present invention provides an electronic endoscope comprising:

a light source for emitting light for illuminating an object to be picked up;

an endoscope probe including a light guide and an image pickup device, the light guide guiding the light from the light source to a tip of the endoscope probe, and the image pickup device picking up the object illuminated by the light emitted from the tip of the endoscope probe;

a test-pattern-chart device including a receptacle for removably holding the tip of the endoscope probe, a plurality of test-pattern charts, and a driving member which has one of the test-pattern charts face the tip of the endoscope probe, and has the light illuminate the facing test-pattern chart so that the image pickup device can pick up the facing test-pattern chart;

a video processor including processing amplifiers to which an output of the image pickup device is supplied;

selection means for selecting one of the test-pattern charts by controlling the driving member; and means for controlling the processing amplifiers by identifying characteristic type of the processing amplifiers corresponding to the test-pattern chart selected by the selection means, by comparing outputs of the processing amplifiers correlated with the identified characteristic with predetermined references, and by controlling the processing amplifiers so that the identified characteristic agree with the predetermined references.

According to the present invention, the electronic characteristics of the processing amplifiers such as white balance, gamma balance, black level, or the like can be automatically adjusted at optimum reference values by automatically selecting one of the plurality of the test-pattern charts in sequence so that the selected test-pattern chart faces the tip of the probe of the endoscope, and by automatically setting the control values of the video processing amplifiers in accordance with the selected chart by means of the auto-setup circuit so that the control values agree with the reference values. Thus, even technicians or doctors who are unfamiliar with the operation of video processors can easily and accurately adjust the color or the like.

The above and other objects, effects, features and advantages of the present invention will become more apparent from the following description of the embodiment thereof taken in conjunction with the accompanying drawings.

BRIEF DESCRIPTION OF THE DRAWINGS

FIG. 4 is a view illustrating a part of the mechanical portion shown in FIG. 1;

FIGS. 5A and 5B are a front view and a side view for illustrating another embodiment of the test-pattern chart of the present invention, respectively.

DETAILED DESCRIPTION OF PREFERRED EMBODIMENTS

The invention will now be described with reference to the accompanying drawings.

Figure 1:
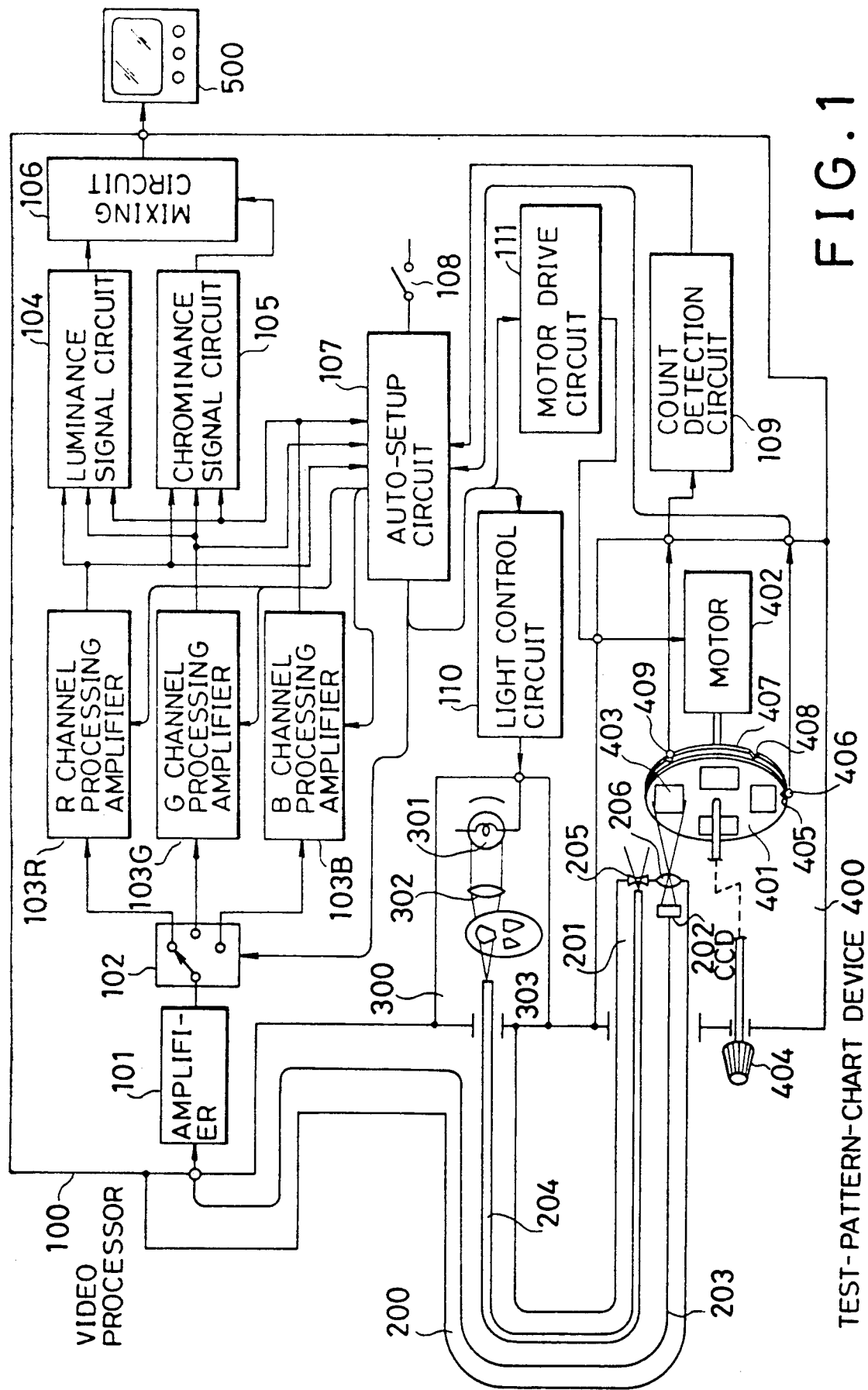
FIG. 1 is a block diagram showing the arrangement of an embodiment of the present invention.

FIG. 1 shows an embodiment of the present invention. In this figure, reference numeral 100 designates a video processor of an electronic endoscope of the present invention, 200, a probe of the endoscope, 300, a light source, 400, a test-pattern-chart device, and 500, a monitor system.

In the video processor 100, reference numeral 101 denotes an amplifier to which an image output from a solid-state image pickup device 202 is supplied via a lead line 203 provided in the probe 200. The solid-state image pickup device 202 which is made of a CCD, for example, is provided at the tip 201 of the probe 200. Reference numeral 102 designates a switch cicruit for switching the R, G and B channel signals produced from the amplifier 101 so as to separate and allocate a path to each of the R, G and B signals. The R, G and B signals are supplied to processing amplifiers 103R, 103G and 103B, respectively. The processing amplifiers adjust the signal levels, pedestals, gamma characteristics, flares, and color temperature correctors, or the like with regard to the R, G and B signals supplied from the switch circuit 102. The outputs of the processing amplifiers 103R, 103G and 103B are fed to a luminance signal circuit 104, a chrominance signal circuit 105, and an auto-set circuit 107. A mixing circuit 106 mixes the outputs of the luminance signal circuit 104 and the chrominance signal circuit 105 to generate a video signal of the NTSC (or PAL or SECAM) system. The video signal produced from the mixing circuit 106 is fed to the monitor system 500.

The auto-setup circuit 107 automatically sets various electrical control values of the respective processing amplifiers 103R, 103G and 103B to their predetermined reference values. Among these control values, are values concerning levels of the video signals, pedestals, gamma correction characteristics, flares, color temperature correctors or the like. To accomplish this, the auto-set up circuit 107, receiving the signals from the processing amplifiers 103R, 103G and 103B, compares the signals with the reference signals thereof, and feeds the compared outputs back to the processing amplifiers so that the control values are set at the reference values. The auto-setup circuit 107 is activated in response to the operation of a start switch 108. A count detection circuit 109 commands the auto-set up circuit 107 to adjust one of the various functions such as white balance, gamma correction, and black level, when the count value reaches a predetermined value. As the auto-setup circuit 107, can be used "a signal amplitude adjusting device for a color television camera" described in Japanese patent application publication No. 50-19410.

Figure 2:
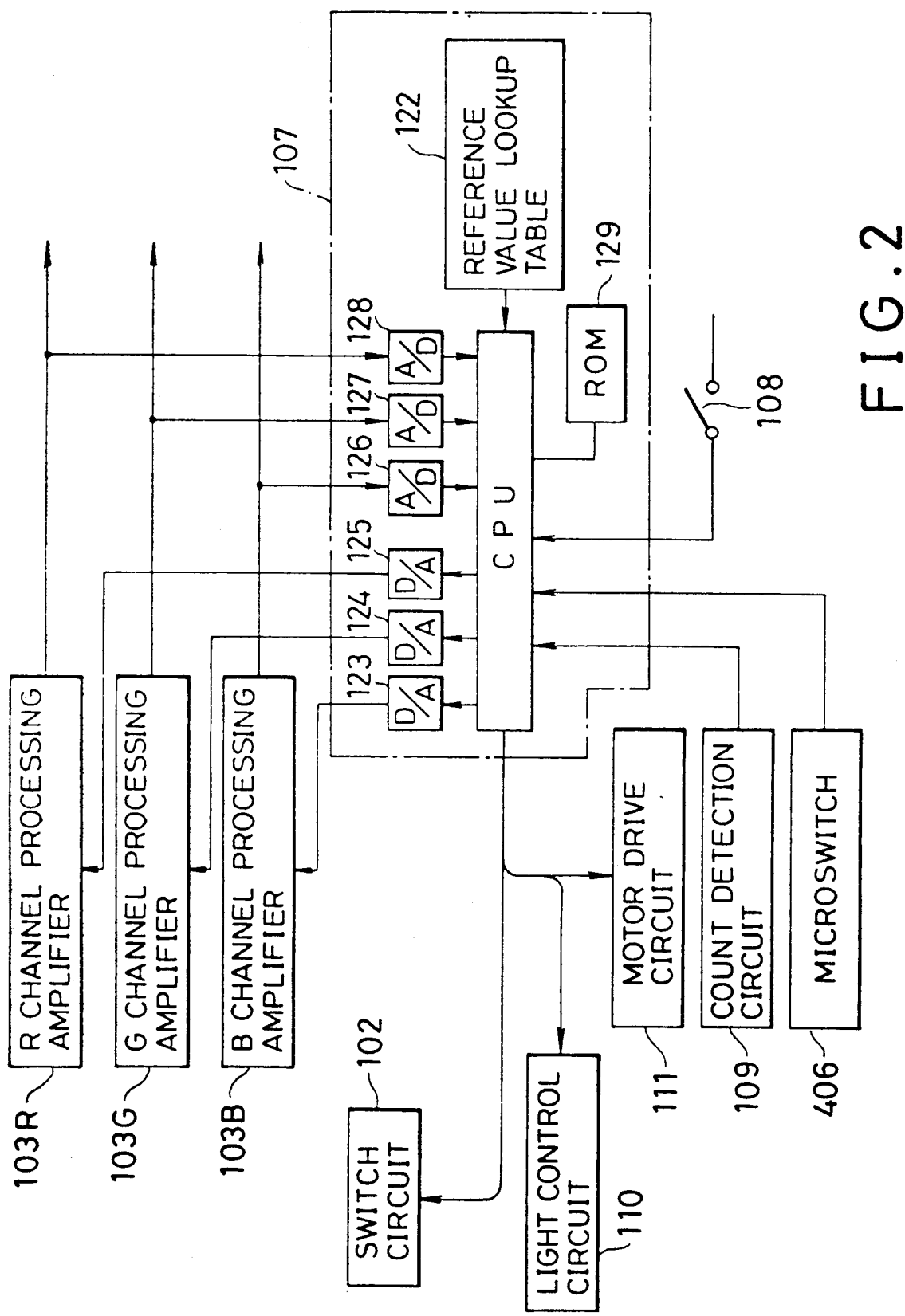
FIG. 2 is a block diagram showing an example of an auto-setup circuit of the embodiment.

FIG. 2 shows an example of the auto-setup circuit 107. In this figure, a CPU (Central Processing Unit) 121 is connected to a reference value lookup table 122. The reference value lookup table 122 stores predetermined digital data (reference values) of various electrical characteristics such as a black level, white balance, gamma balance, flare, color temperature correctors, video signal level, or the like, for each channel of the R, G and G. These digital data are supplied to D/A converters 123-125 via the CPU 121, and are converted to analog signals which are supplied to the processing amplifiers 103R, 103G and 103B. The outputs of the processing amplifiers are supplied to A/D converters 126-128 which convert the outputs to digital data and supply the data to the CPU 121. An ROM 129 stores a control program of the CPU 121.

Figure 6:
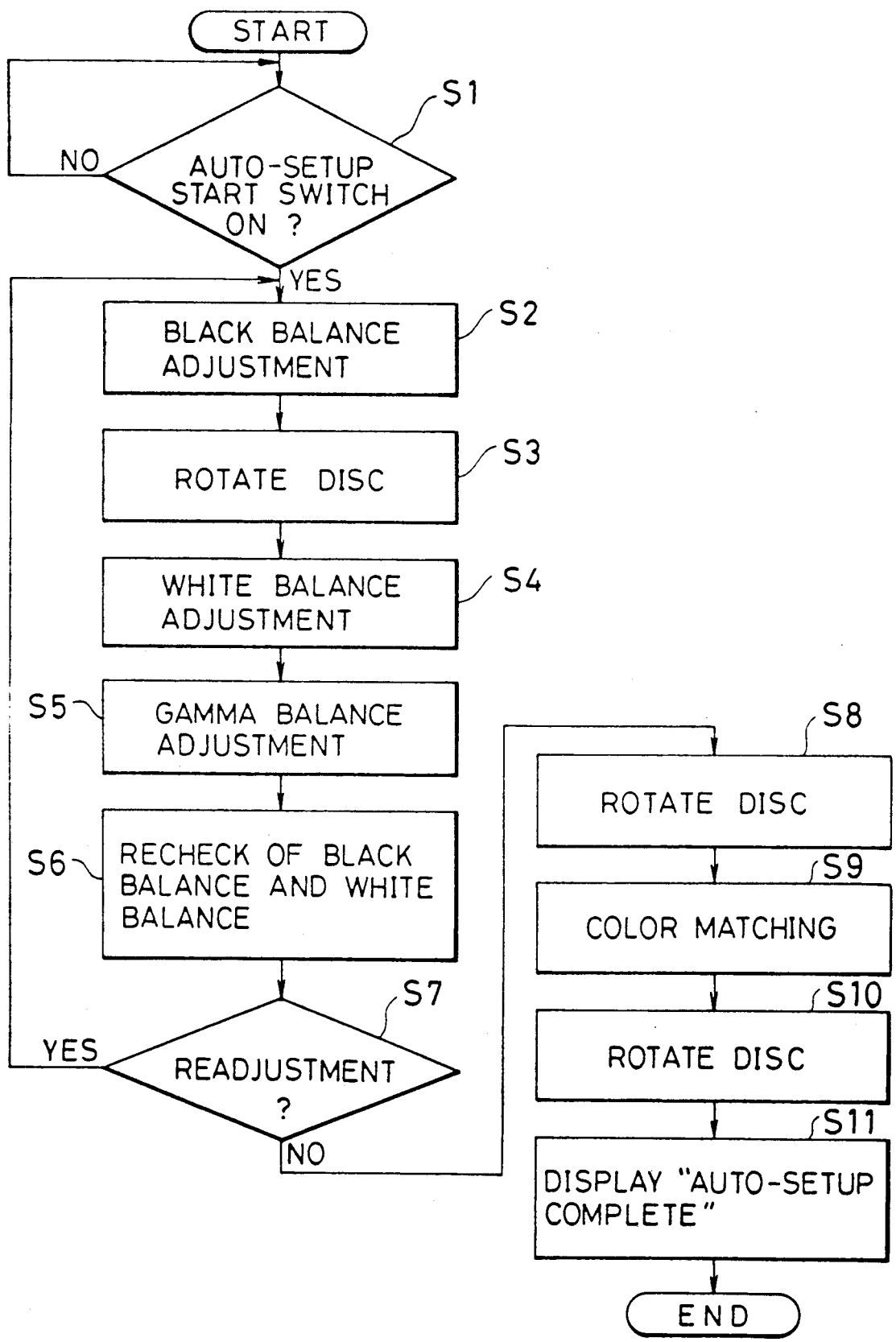
FIGS. 6 and 7 are flowcharts showing an example of control procedure of the auto-setup circuit.
Figure 7:
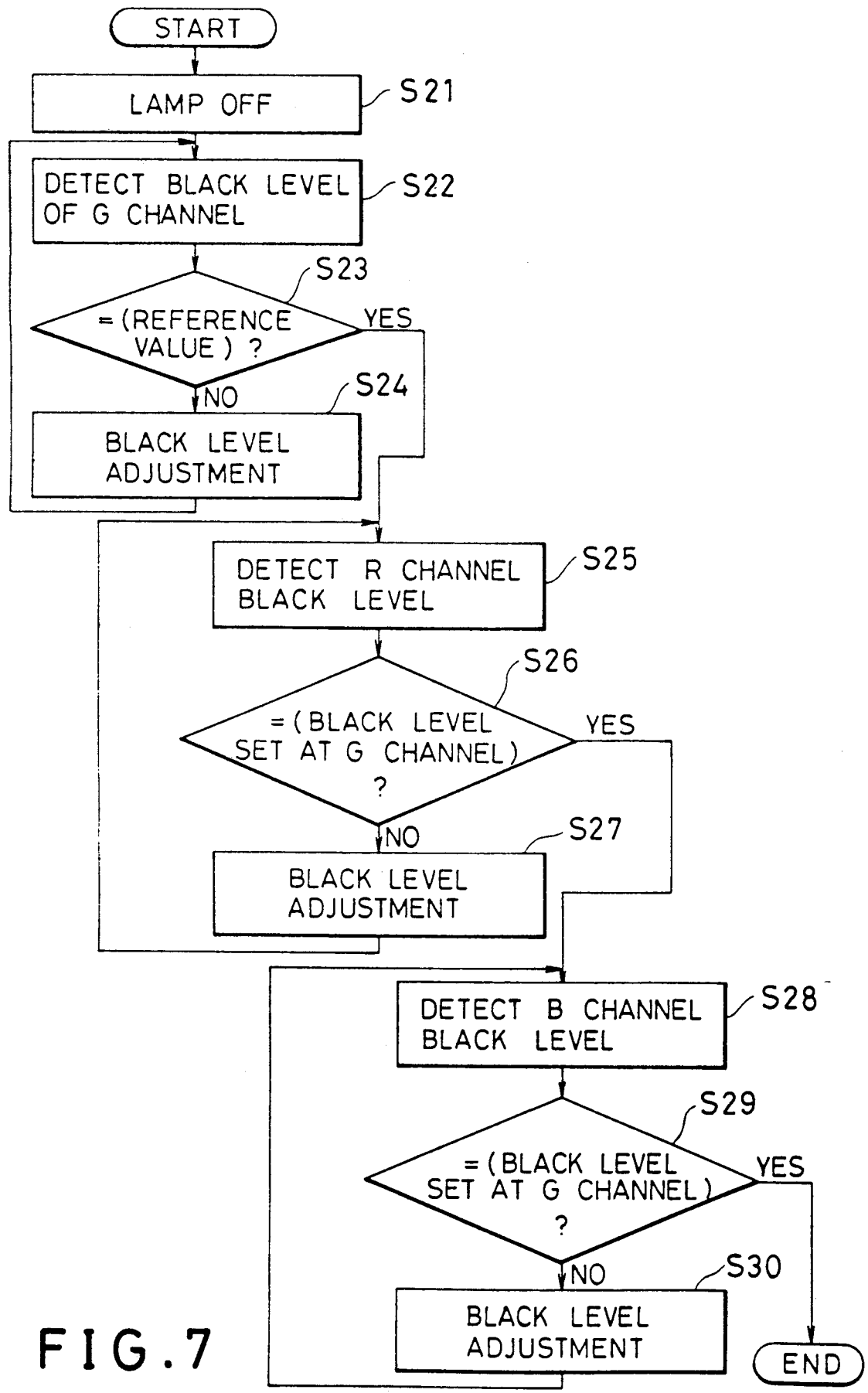

The control program is arranged along the flow illustrated in flowcharts shown in FIGS. 6 and 7.

FIG. 6 shows a general procedure of the program. The program is started when the start switch 108 is activated at step S1. At step S2, the black balance is adjusted witha lamp 301 turned off. More specifically, the black level of each processing amplifier is compared with the corresponding reference value, and the feedback control operates so that the black level is set at the reference value.

After the black levels are adjusted at the reference value, the CPU 121 recognizes it, and proceeds to the next step S3. At step S3, the CPU 121 drives a motor 402 so that the test-pattern chart for the grey scale faces the tip 201 of the probe 200 of the endoscope.

In this condition, white balances and gamma balances are successively adjusted at steps S4 and S5, respectively: the processing amplifier of each channel undergoes the feedback control so that the white level is set at the reference value and the gamma characteristics are set at the reference characteristics.

Subsequently, at step S6, the black balances and white balancea are rechecked. As a result, if readjustment is required, the processing returns from step S7 to step S2. In contrast, if the readjustment is not required, the processing proceeds from step S7 to step S8 at which a disc 401 is rotated. Thus, when the processing amplifiers are set at the reference values and the reference characteristics, the CPU 121 recognizes this, and drives the motor 402 again at step S8 so that the next test-pattern chart, that is, a color chart will face the tip 201. After that, the CPU 121 carries out the color matching processing as step S9.

When the color matching has been completed, the CPU 121 recognizes this, and drives the disc 401 at step S10 so that a picture of face/internal organ (including the blood), or instead, an imitation of an internal organ or the like will face the tip 201 of the endoscope probe 200. In this condition, an imitation or a picture is picked up, and the image thereof undergoes a visual inspection. In parallel with this, the CPU 121 proceeds to step S11 at which a phrase reading "complete auto-setup" is displayed on the monitor system 500. Thus, the entire procedure is completed.

According to the predetermined sequence of adjustment items, the processings such as adjustment of the processing amplifiers, detection of completion of the adjustment, and selection of the next test-pattern chart, are repeated until all the adjustment items are finished.

Returning to FIG. 1 again, reference numeral 110 designates a light control circuit for controlling the lamp 301 in the light source 300, and reference numeral 111 denotes a motor drive circuit for driving the motor 402 that rotates the test-pattern-chart disc 401 in the test-pattern-chart device 400.

The switch circuit 102, light control circuit 110, and the motor drive circuit 111 are also controlled by the auto-setup circuit 107 so that switching timing among the channels, on/off timing of the illumination, and on/off timing of driving the motor 402 are correctly determined.

In the light source 300, white light produced from the lamp 301 is concentrated by a condenser lens 302 and is transmitted through a color filter 303 to produce a color image signal. The color filter 303 includes R, G and B areas radially disposed on the disc at fixed intervals, and produces one of the R, G and B light rays by sequentially transmitting the light from the lens 302 through the R, G and B areas. The output light is guided to the tip 201 via the light guide 204 of the endoscope probe 200. At the tip 201, an illumination lens 205 is provided to diverge the light beam. The diverged light illuminates one of the test-pattern charts 403 on the disc 401.

The endoscope probe 200 is arranged by a fiber bundle tube of a minimal diameter (for example, a diameter of about 6-10 mm) considering that it may be used to pick up the inside of a small body cavity. The solid-state image pickup device 202 should also be made as small as possible.

In the test-pattern-chart device 400, the disc 401 can be driven either by the motor 402 or by a test-chart-pattern-switching knob 404 which is manually operated so that a desired test-pattern chart 403 faces the solid-state image pickup device 202 through the objective lens 206.

Figure 3:
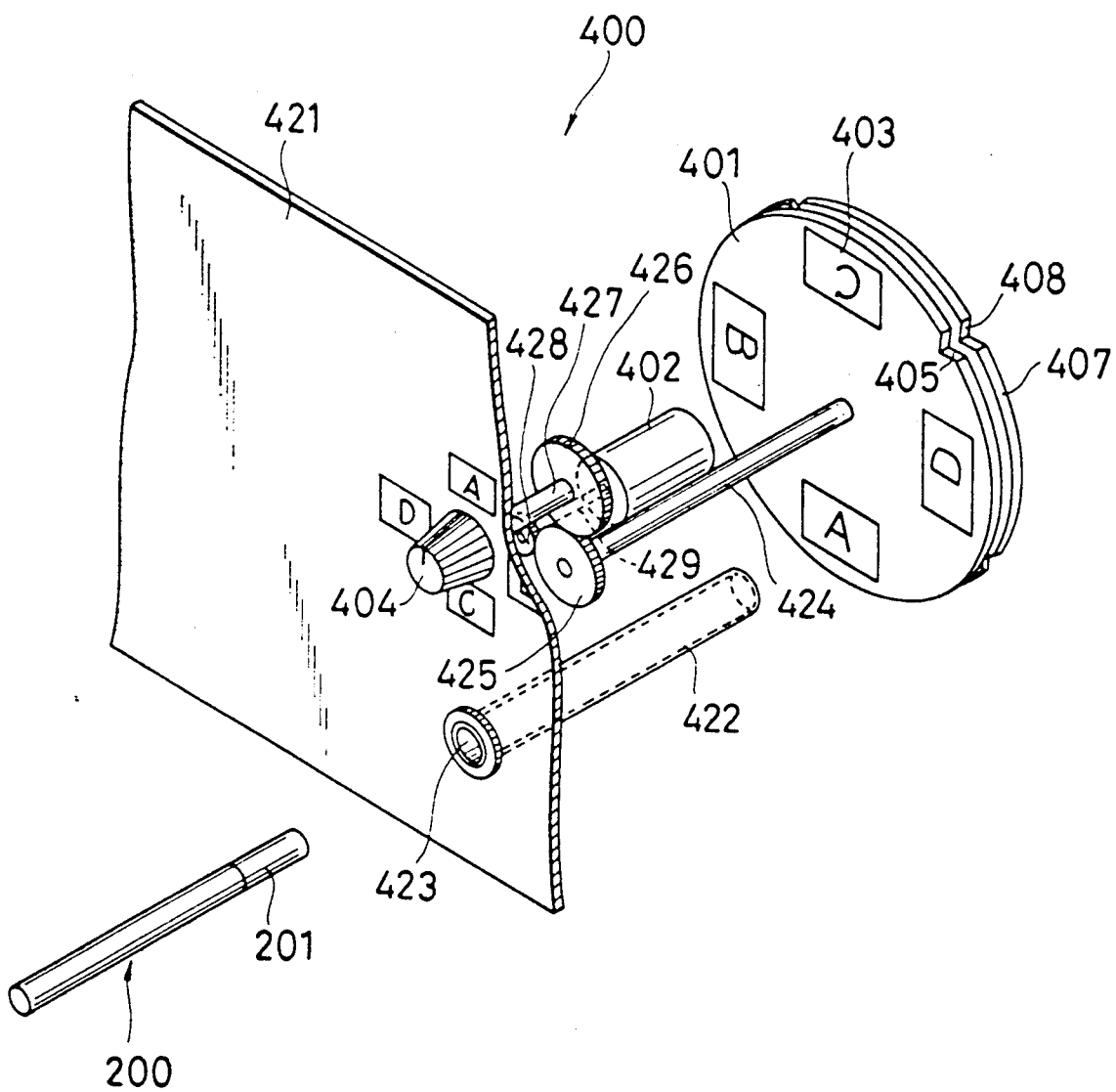
FIG. 3 is a perspective view illustrating details of the mechanical portion shown in FIG. 1.

Incidentally, the tip 201 of the endoscope probe 2000 is made freely attachable to and removable from the test-pattern-chart device 400 as shown in detail in FIG. 3. The tip 201, when attached to the test-pattern-chart device 400 as shown in FIG. 1, illuminates the test-pattern chart 403 by the lilght from the lens 205, and the reflected light by the test-pattern chart is received by the solid-state image pickup device 202 via the lens 206.

As shown in FIG. 4, the disc 401 is provided with a notch 405 on its circumference to indicate the initial position at which the disc 401 initially stops when the motor 402 begins to rotate, that is, the position corresponding to the first test-pattern chart. In addition, a microswitch (snap-action switch) 406 is provided at the circumference of the disc 401 so that the microswitch 406 is turned on by the notch 405. The output of the microswitch 406 is supplied to the auto-setup circuit 107 so as to select the first test-pattern chart and stop the motor 402.

To the disc 401, a disc 407 is coupled with their axis in common. The disc 407 has a plurality of notches 408 each corresponding to one of the test-pattern charts 403. In addition, a second microswitch 409 is provided at the circumference of the disc 407 so that the microswitch 409 is turned on at the notch positions. The output of the microswitch 409 is supplied to the count detection circuit 109 which generates a position detection output that indicates the respective positions of a plurality of the test-pattern charts 403. The position detection output is supplied to the auto-setup circuit 107 which sets various adjusting values to the processing amplifiers 103R, 103G and 103B in accordance with the test pattern charts.

Thus, various adjustments such as white balance, gamma balance, black level or the like of the video processor can be automatically and sequentially performed, and these adjusting values are set at their reference values. Accordingly, even technicians or doctors who are not specialists in the video processor adjustment can devote into their own work without bothered by the adjustment of the video processors.

FIG. 3 shows a detailed example of the mechanism of the test-pattern-chart device 400. In this figure, reference numeral 421 designates a panel inside the back of which is provided a probe guide pipe (a receptacle) 422 with an insertion opening 423 on the panel 421. The probe guide pipe 422 has a slightly larger inner diameter than the outer diameter of the tip 201 of the endoscope probe 200 so that the probe 200 can be freely inserted to or extracted from the probe guide pipe 422. The tip 201 of the endoscope probe 200 is inserted into the probe guide pipe 422 until the test-pattern chart 403 is correctly reproduced on the screen of the monitor system 500.

The common axis 424 of the second disc 407 and the disc 401 to which a plurality of test-pattern charts 403 are attached, is linked to an axis 427 by two gears 425 and 426. The axis 427 is joined to the test-pattern-chart-switching knob 404 provided on the panel 421 so that a desired test-pattern chart 403 can be manually selected by the knob 404. The gear 425 is further linked to an axis 429 via a gear 428. The axis 429 is joined to the motor 402. Accordingly, the test-pattern charts 403 are rotated by the motor 402 so that one of the test-pattern charts 403 is automatically and sequentially selected in a predetermined sequence.

Incidentally, although the motor 402 is located at the opposite side of the knob 404 with regard to the disc 401 as shown in FIGS. 1 an 4, they may be located at the same side as shown in FIG. 3. Anyway, any arrangement can be permitted as long as the disc 401 can be rotated either manually by the knob or automatically by the motor.

In FIG. 3, the probe guide pipe 422 must be placed at such a position that satisfies the following conditions: first, the light transmitted through the light guide 204 and emitted from the tip 201 should illuminate the selected test-pattern chart 403; and the solid-state image pickup device 202 at the tip of 201 should correctly receive the reflected light from the test-pattern chart. If the light illuminating the test-pattern chart 403 illuminates other than the test-pattern chart 403, and the reflection light therefrom enters the solid-state image pickup device 202, correct adjustment by the auto-setup circuit 107 becomes difficult. For this reason, areas on the disc 401 except the test-pattern charts 403 are preferably coated by a material that can prevent or reduce reflection, that is, by a highly absorbent material. These materials may be affixed to the areas.

Incidentally, although four test-pattern charts 403 are disposed on the disc 401 in FIG. 3, the number of the charts is not limited to four; it can be determined at a suitable number in accordance with intended adjusting items.

As the test-pattern charts 403, charts other than of common planar structure can be used: for example, as shown in FIGS. 5A and 5B, a pincushion test-pattern chart 441 can be used which is arranged by affixing a chart on the concave surface of a concave structure 440. The pincushion test-pattern chart 441 of this type can be appropriately used to adjust a barrel image which is produced when a fish-eye lens is used as the objective lens 206 provided at the tip 201 of the endoscope probe 200. The pincushion test-pattern chart 441 can also be preferably used when a barrel image is reproduced or the four corners of an image are blurred even when a common lens is used as the objective lens 206.

Next, the operation of the instrument of the present invention will be described.

As indicated by step S1 of FIG. 6, when the start switch 108 is turned on, the processing proceeds to step S2 at which the black balance is set. The adjustment of the black balance is performed according to the control sequence as shown in FIG. 7. At step S21, the incident light to the solid-state image pickup device 202 is turned off by supplying an illumination off signal from the auto-setup circuit 107 to the lamp 301 via the light control circuit 110. In this condition, the processing amplifiers 103R, 103G and 103B for respective channels exchange data and control signals with the auto-setup circuit 107 to set the black levels of the R, G and B channels. Thus, the black correction circuits of the processing amplifiers 103R, 103G and 103B are automatically controlled.

FIG. 7 shows an example of the black level set procedure. As shown in this figure, the black level of the G channel is detected at step S22, and the detected black level is compared with a predetermined reference value at step S23. If the two disagree, the processing returns to step S22 to carry out a similar processing after adjusting the black level at step S24. If the actual G channel black level agrees with the reference value, the processing proceeds to step S25. At steps S25-S27, and steps S28-S30, the black levels of the R and B channels are adjusted, respectively, so that they agree with the G channel black level by using the set G channel black level as a reference.

Next, the white balances and gamma balances are set. First, at step S3, the disc 401 is rotated until the test-pattern chart of the grey scale appears as an image signal by controlling the motor 402 by the auto-setup circuit 107 via the motor drive circuit 111. When the test-pattern chart of the grey scale correctly appears, the microswitches 406 and 409 contacting the discs 401 and 407 turn on, and supply the auto-setup circuit 107 with an answer signal to stop the motor 402.

When the grey scale test pattern chart appears as the image signal, the processing proceeds to the next steps S4 and S5. At these steps, the processing amplifiers of R, G and B channels exchange data and control signals with the auto-setup circuit 107, and automatically control the white level correction circuits and gamma correction circuits of the respective channels to adjust the white balances and gamma balances.

An example of a setting method of the white levels and the gamma characteristics is as follows: first, the white level and gamma characteristic of the G channel are set at predetermined values in a manner similar to the adjustment of the black level; then the white levels and gamma characteristics of the R and B channels are adjusted so that they agree with the white level and gamma characteristic of the G channel by using the white level and gamma characteristic of the G channel as references.

After rechecking the need of readjustment of the black balance and white balance at steps S6 and S7, the disc 401 is rotated by supplying the motor 402 with a rotation signal until the next test-pattern chart, that is, a color chart for color matching adjustment appears.

When the color chart appears, only the switch 409 contacting the disc 407 turns on, and stops the motor 402 by supplying the auto-setup circuit 107 with an answer signal via the count detection circuit 109. The count detection circuit 109 counts the number of notches 408 of the disc 407 so that an intended test-pattern chart is produced as an image signal.

When the test-pattern chart of the color chart appears as the image signal, the processing proceeds to the next step S9. At step S9, the processing amplifiers 103R, 103G and 103B exchange the data signal and control signal with the auto-setup circuit 107, and automatically control the color temperature corrector circuit so that the image assumes a color which a maker or a user prestored.

As two other test-pattern charts on the disc 401, pictures of face/internal organs (including blood) are disposed, or otherwise, imitations of internal organs are disposed instead of the test-pattern charts.

When the color matching is completed at step S9, the processing proceeds to step S10 at which the motor 402 is stopped by a command from the auto-setup circuit 107. In this condition, the above-mentioned test-pattern charts are sequentially visually inspected. Simultaneously, at the next step S11, a phrase reading "complete auto-setup" is displayed on the screen of the monitor system 500. When the result of the visual inspection is not satisfactory, the above adjustments can be repeated by turning on the start switch 108 again. Thus, the best image can be reproduced even by a technician or a doctor unfamiliar with video processors.

Although a specific embodiment of an electronic endoscope constructed in accordance with the present invention has been disclosed, it is not intended that the invention be restricted to either the specific configurations or the uses disclosed herein. Modifications may be made in a manner obvious to those skilled in the art. For example, the mechanical portion shown in FIG. 3 can be incorporated into a separate case from the body of the electronic endoscope so that it can be used outside the endoscope. Accordingly, it is intended that the invention be limited only by the scope of the appended claims.

What is claimed is:

1. An electronic endoscope comprising:
    a light source for emitting light for illuminating an object to be picked up;
    an endoscope probe including a light guide and an image pickup device, the light guide guiding the light from the light source to a tip of the endoscope probe, and the image pickup device picking up the object illuminated by the light emitted from the tip of the endoscope probe;
    a test-pattern-chart device including a receptacle for removably holding the tip of the endoscope probe, a plurality of test-pattern charts, and a driving member which has one of the test-pattern charts face the tip of the endoscope probe, and has the light illuminate the facing test-pattern chart so that the image pickup device can pick up the facing test-pattern chart;
    a video processor including processing amplifiers to which an output of the image pickup device is supplied;
    selection means for selecting one of the test-pattern charts by controlling the driving member; and
    means for controlling the processing amplifiers by identifying characteristic type of the processing amplifiers corresponding to the test-pattern chart selected by the selection means, by comparing outputs of the processing amplifiers correlated with the identified characteristic with predetermined references, and by controlling the processing amplifiers so that the identified characteristic agree with the predetermined references.

2. An electronic endoscope as claimed in claim 1, further comprising means for commanding the selection means to select another test-pattern chart when the controlling means completes adjustment to have the identified characteristic agree with the predetermined references with regard to the selected test-pattern chart.

3. An electronic endoscope as claimed in claim 1, wherein the test-pattern charts include a pincushion test-pattern chart.

4. An electronic endoscope as claimed in claim 1, wherein the light source and the test-pattern-chart device are incorporated into the video processor.

5. An electronic endoscope as claimed in claim 4, further comprising means for commanding the selection means to select another test-pattern chart when the controlling means completes adjustments to have the identified characteristic agree with the predetermined references with regard to the selected test-pattern chart.

* * * * *